United States Patent [19]

Kushner et al.

[11] 4,052,904
[45] Oct. 11, 1977

[54] APPARATUS FOR OBTAINING A RELATIVELY PARTICLE-FREE SAMPLE OF A LIQUID

[75] Inventors: Jack Kushner, Lindenhurst; Henry G. Zwirblis, Nesconset, both of N.Y.

[73] Assignee: Delta Scientific Corporation, Lindenhurst, N.Y.

[21] Appl. No.: 635,981

[22] Filed: Nov. 28, 1975

Related U.S. Application Data

[63] Continuation-in-part of Ser. No. 501,875, Aug. 30, 1974, Pat. No. 3,999,945.

[51] Int. Cl.² ............................................. G01N 1/20
[52] U.S. Cl. ............................. 73/421 R; 73/61.1 R
[58] Field of Search ........... 73/421 R, 421 B, 61.1 R; 340/236; 210/85, 400, 402, DIG. 25

[56] References Cited

U.S. PATENT DOCUMENTS

| | | | |
|---|---|---|---|
| 3,800,219 | 2/1974 | Fosberg | 340/236 X |
| 3,905,902 | 9/1975 | Hoegberg et al. | 210/DIG. 25 |
| 3,916,674 | 11/1975 | Miller et al. | 73/61.1 R |

FOREIGN PATENT DOCUMENTS

| | | | |
|---|---|---|---|
| 1,399,477 | 4/1965 | France | 340/236 |

Primary Examiner—Richard C. Queisser
Assistant Examiner—Joseph W. Roskos
Attorney, Agent, or Firm—Pennie & Edmonds

[57] ABSTRACT

A device for obtaining a relatively particle-free sample of liquid is disclosed. The device comprises a rotatable member having a planar fluid wettable collection surface. The rotating member is disposed within a trough through which a portion of the liquid to be tested passes, thereby resulting in the formation of a thin film of the liquid on the collection surface of the rotating member as it emerges from the liquid. A blade which bears against the collection surface is used to remove the liquid. In accordance with the preferred embodiment, a baffle is provided for deflecting particles floating on the surface of the liquid inside the trough away from the collection surface of the rotating member.

6 Claims, 6 Drawing Figures

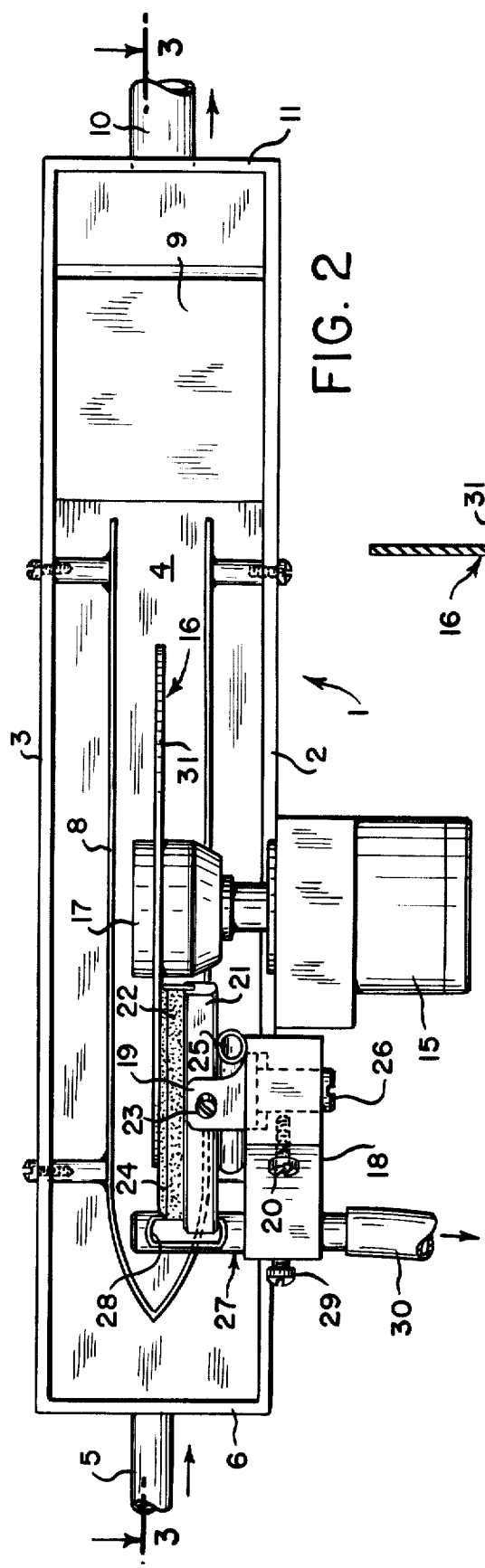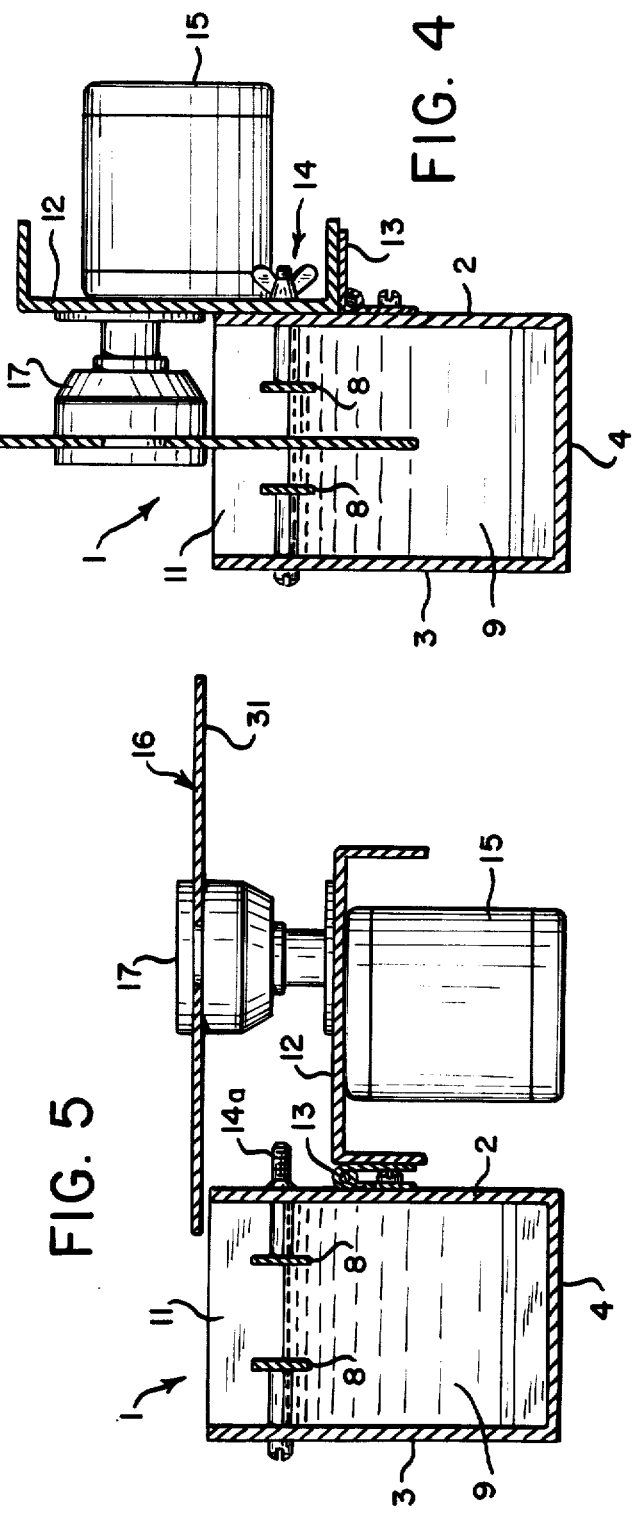

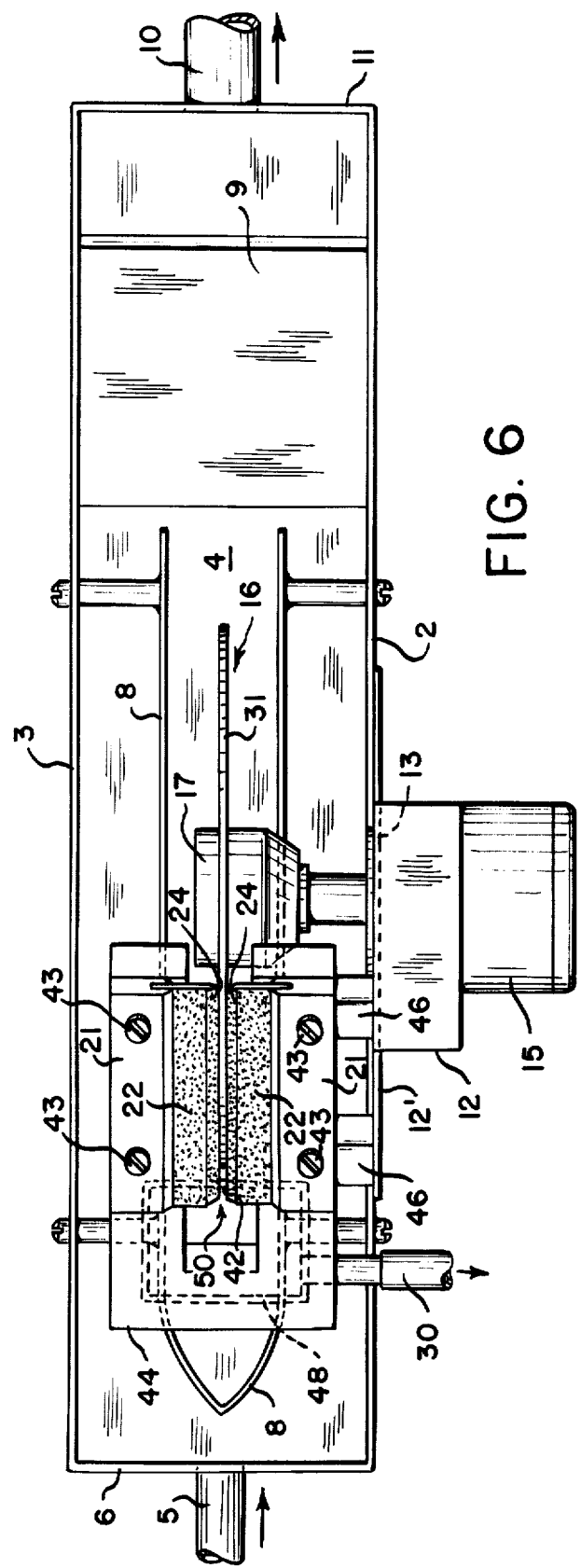

4,052,904

APPARATUS FOR OBTAINING A RELATIVELY PARTICLE-FREE SAMPLE OF A LIQUID

CROSS-REFERENCE TO RELATED APPLICATION

This application is a continuation-in-part of our copending U.S. patent application Ser. No. 501,875 filed Aug. 30, 1974 entitled "Liquid Analysis System", now U.S. Pat. No. 3,999,945.

BACKGROUND OF THE INVENTION

With increasing public concern over the quality of the environment, a significant need has arisen for equipment which is capable of accurately and economically testing various environmental conditions. The present invention, while suitable for employment in any system performing automated chemical analysis, is particularly useful for continuously and automatically obtaining a relatively particle-free sample of liquid from a body of water, such as a lake, stream or municipal water supply.

Conventionally, it one wishes to measure the level of pollutant, the biological oxygen demand or some ohter parameter of a body of water, one would take a sample of the water and submit it to an appropriate quantitative chameical analysis. These chemical tests generally comprise a number of steps involving the mixing and reacting of a predetermined amount of the sample or reacted sample with specific quantities of various chemical reagents.

These tests are best carried out individually by relatively highly skilled personnel. Naturally, if one wishes to use a test to obtain data continuously or at frequent intervals and thus construct an accurate and complete picture of the state of water quality over a period of time, conventional manual testing is quite expensive. Moreover, if one desires to perform a continuous analysis with automated equipment, it is necessary to have a technique for taking a continuous sample. Simply diverting a portion of a liquid from the body will not provide acceptable results because the thus obtained sample tends to include solid particles which interfere with the proper operation of automatic analysis equipment.

SUMMARY OF THE INVENTION

The present invention is directed toward an apparatus for obtaining a pure sample of a liquid to be tested and subjected to a quantitative chemical analysis. Such sampling is performed automatically and continuously by the apparatus of the present invention. The apparatus of the present invention is particularly advantageous due to the relatively small amount of maintenance required and the compact, dependable and relatively simple nature of the apparatus.

The liquid sample is obtained by continuously submerging a surface in the liquid and collecting the thin liquid film which tends to adhere to that surface. In the preferred embodiment, a rotating disc is partially submerged in a trough through which a portion of the liquid to be sampled is continuously flowing. As the disc rotates in the liquid, the film of liquid that forms on its side surface is continuously removed by a blade or pair of blades which bear against the surface of the disc and sent from the sample via a tube to the analysis apparatus. Light particles are prevented from being taken up by the wheel through the provision of a deflector positioned upstream of the disc and partially submerged in the flowing liquid. Heavy particles such as sand are generally not caught by the wheel due to the fact that they tend to sink to the bottom of the trough. They are prevented from collecting there by the provision of a slit at the bottom of the trough downstream from the disc through which they are allowed to pass. In accordance with the present invention, the liquid sample thus obtained has been found to be of sufficient clarity and purity for most monitoring systems. However, under special circumstances, further purification and clarification may be advantageous.

BRIEF DESCRIPTION OF THE DRAWINGS

FIG. 2 is a plan view of the sampling device shown in FIG. 1;

FIG. 4 is a vertical section taken along line 4—4 of FIG. 1;

FIG. 5 is a figure similar to FIG. 4 showing the sampling disc in the retracted position rotated 90° for cleaning of the trough; and FIG. 6 is a top plan view of an alternative embodiment of the liquid sampling device.

DETAILED DESCRIPTION OF THE PREFERRED EMBODIMENT

Figure 1:
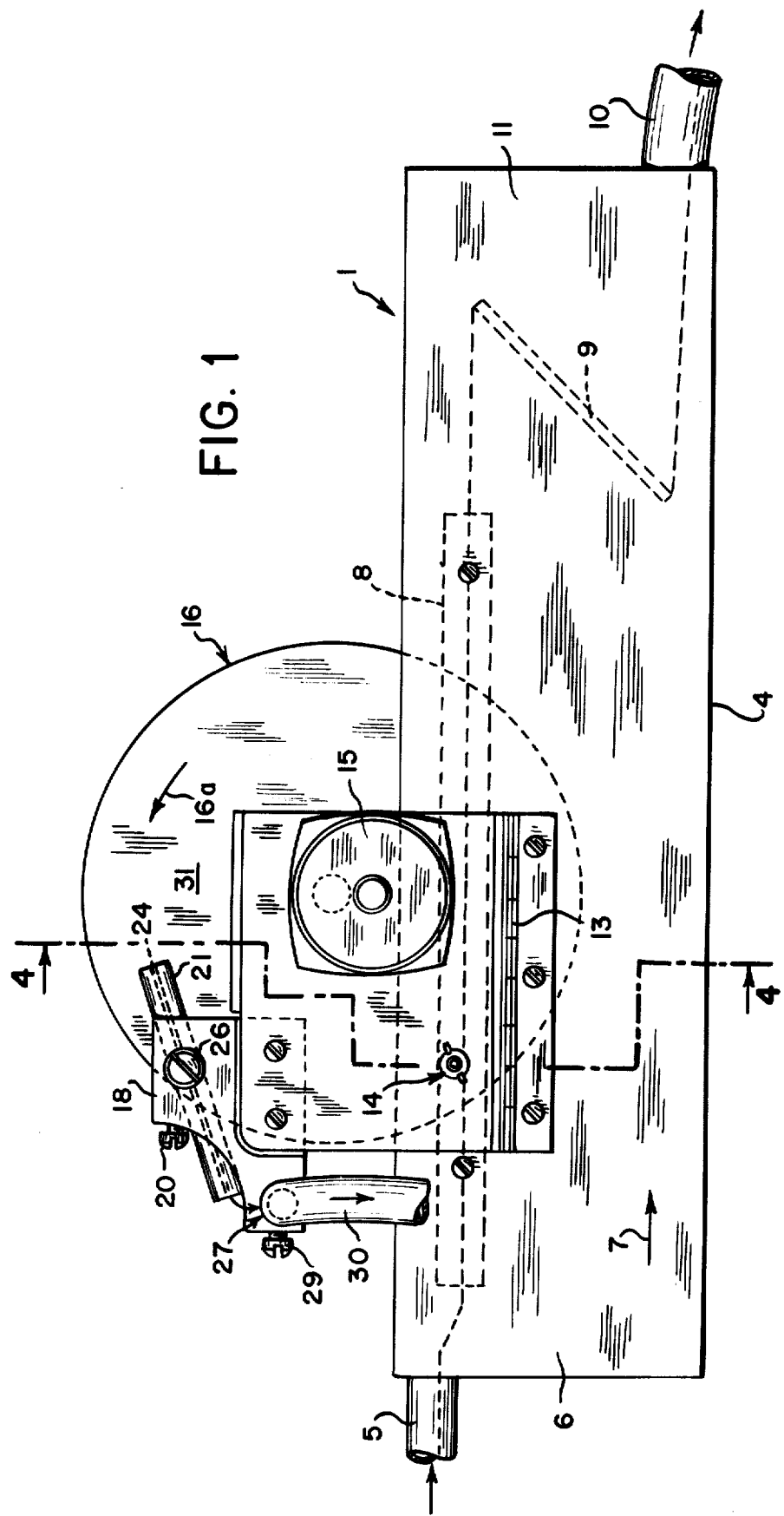
FIG. 1 is a side view of a liquid sampling device constructed in accordance with the present invention.
Figure 3:
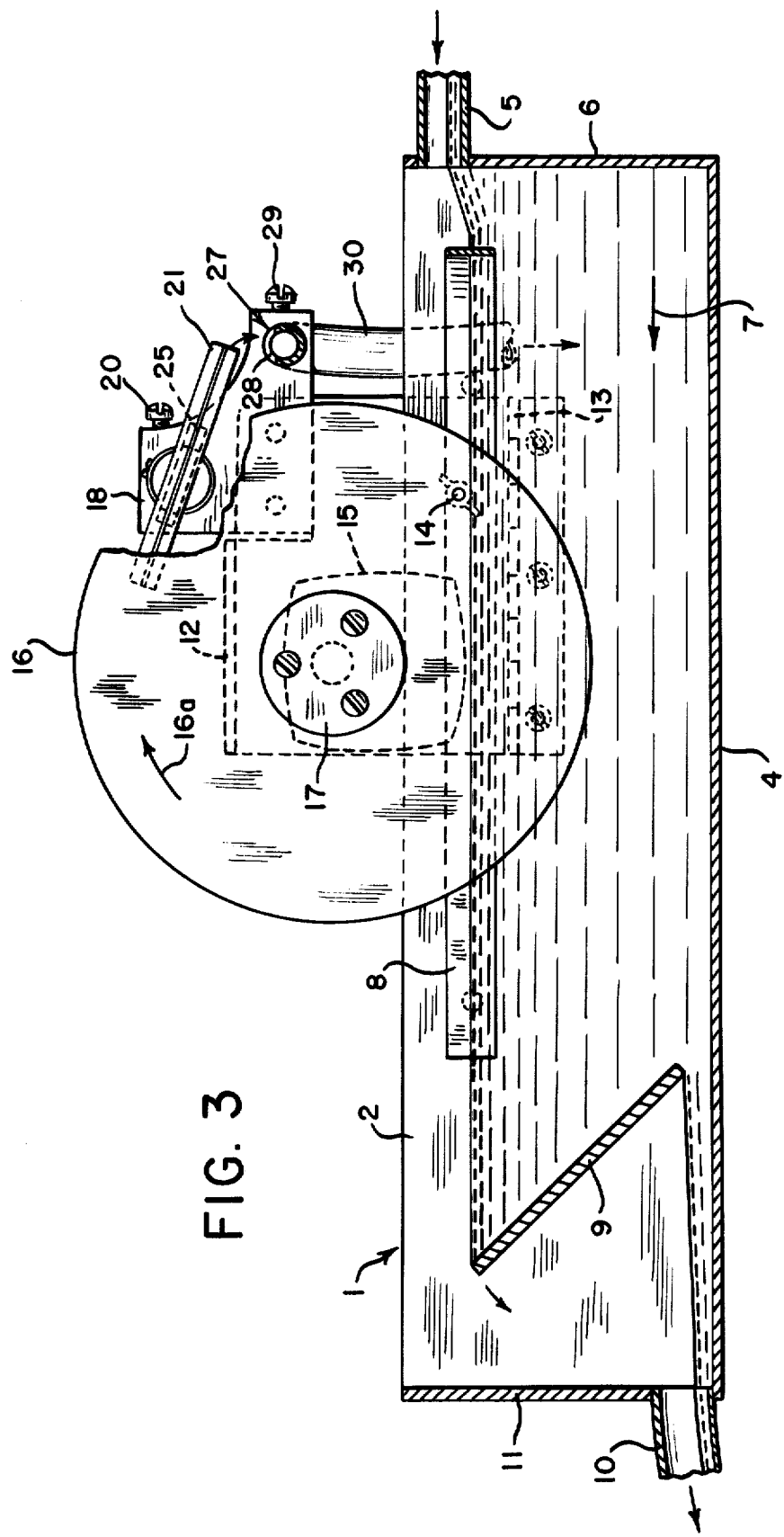
FIG. 3 is a longitudinal secion taken along line 3—3 of FIG. 2.

Referring to FIGS. 1-4, a portion of a liquid to be tested is diverted and caused to flow continuously through the sampling device 1. Sampling device 1 comprises a trough having a pair of sidewalls 2 and 3 secured to a bottom member 4. Liquid enters the trough through inlet conduit 5 in a front retaining wall 6 and travels through the trough in the direction indicated by arrow 7. Lighter particles which float on the surface of the liquid in the trough are deflected and thus prevented from entering the system by a partially submerged baffle 8 secured to sidwalls 2 and 3. These lighter particles thus follow a path over the top of a slanted rear wall 9. Heavier particles are carried along the bottom of the trough and exit through the aperture defined by the bottom of the slanted rear wall 9 and bottom member 4. An exit conduit 10 is mounted on a rear wall 11 for disposal of the liquid after it has passed through the sampling device.

The sampling mechanism is mounted on a support plate 12 which is secured to the sidewall 2 of the trough by a hinge 13 and bolt and wing-nut assembly 14. The bolt 14a is mounted in sidewall 2 of the trough. Removal of the wing-nut from the bolt allows the support plate to be pivotally displaced (FIG. 5), thus permitting cleaning of the trough. A motor 15 is bolted to support plate 12. A disc 16 is mounted on the shaft of motor 15 through the use of a conventional mounting assembly 17. This disc rotates in the direction indicated by arrow 16a.

Also, secured to support plate 12 is a sampling assembly support block 18. Mounted on support block 18 is a clevis 19 which is set at the desired position by a set screw 20. A wiper blade assembly comprising a support bar 21 and a conventional wiper blade 22, such as that used in an automobile, is secured to clevis 19 by a bolt 23. Insofar as it is desirable to have the wiping surface 24 of blade 22 just barely in contact with the surface of disc 16, a hole (not shown) in support bar 21 through which bolt 23 passes is either somewhat larger in diameter than bolt 23 or elongated in shape. This allows the wiper blade to be urged into the proper position by spring means 25 may simply be a piece of flexible plastic tubing. Clevis 19 is also provided with an adjustment slot 26, which makes adjustment of the angular position of the clevis quite convenient.

The blade is located to bear against the exposed portion of the disc where the latter is rotating in a direction having a downward component. When in wiping engagement against the disc 16, the wiper blade is disposed at an angle to the horizontal with its lower end located beyond the periphery of the disc. An angle of 12° relative to the horizontal is shown with the embodiment of FIGS. 1-5. Situated underneath the lower end of the wiper blade assembly is a receiving or collection tube 27 having an opening 28 which is mounted on the support block 18. The position of collection tube 27 is maintained by a set screw 29. Liquid collected in the collection tube is sent for analysis or further purification via a conduit 30.

In use, liquid proceeds through the trough in the direction indicated by arrow 7 in FIG. 1. Liquid accumulates in the trough and overflows rear wall 9. A small clearance is maintained between rear wall 9 and the bottom 4 of the trough, for allowing the heavy particles to exit below wall 9. Disc 16 rotates and its side surface 31 is thus coated with a thin film of the liquid. If the tangential velocities of submerged points on the disc's surface are less than the flow velocity through the trough, in some cases the likelihood of the disc's picking up impurities is reduced. The thin film is doctored from surface 31 by blade 22 which may be made of rubber or any other suitable material. The collected liquid runs down along the blade to its lower end. It then drops into the receiving or collection tube 27 from which is proceeds via conduit 30 to the next stage of the system. Floating particles are kept from reaching the disc by passing around baffle 8 and over the top of rear wall 9. Excess liquid passing both above and below rear wall 9 of the trough exits via conduit 10 from which it may be sent to a drain or returned to the body of liquid which is being sampled.

An alternative embodiment of the present invention is illustrated in FIG. 6 wherein parts performing identical functions have been given the same reference numerals that they have in the embodiment illustrated in FIGS. 1-5. The primary distinguishing feature of this embodiment is the provision of two wiper blades 22. The use of two wiper blades results in the collection of liquid film which accumulates on both surfaces of disc 16. This embodiment is particularly advantageous insofar as it not only results in the collection of liquid from both surfaces of disc 16 but also collects that liquid more efficiently. As seen in FIG. 6, the blades form a gap 42 between their wiping surfaces 24. This gap is equal to the thickness of the disc 16. Where the blades are aligned opposite the side of the disc, this gap is closed. However, beyond the periphery of the disc, the gap is open. Since, however, a very thin disc, on the order of about 1/16 of an inch is used, the gap is sufficiently small to prevent liquid collected by the wiper blades from dripping off between the blades as it rolls toward the lower ends 50 thereof. In effect, the liquid bridges across the gap and rolls of the ends of the blades. As with the embodiment of FIGS. 1-5, the angle of the blades 22 in double blade construction of FIG. 6 is about 12° relative to the horizontal. Thus, the arrangement shown in FIG. 6 is capable of collecting significantly more than twice the liquid which may be collected by the apparatus illustrated in FIGS. 1-5.

Blades 22 are supported by screws 43 which pass into U-shaped block 44. Block 44, in turn, is secured to an extension 12' of support plate 12 by a pair of support blocks 46. Liquid carried by the two wiper blades 22 is collected by cup 48 after passing over the lower ends 50 of the blades. Cup 48 is secured to the bottom of U-shaped block 44. Output conduit 30 is secured to and in communication with cup 48.

The liquid output of the sampling device is generally suitable for analysis and may be sent directly to an analyzing apparatus such as that disclosed in our copending U.S. patent application Ser. No. 501,875 filed Aug. 30, 1974 and entitled "Liquid Analysis System".

We claim:

1. In an apparatus for obtaining a sample of a liquid and having a disc with a planar fluid wettable side surface and means for rotating said disc with the peripheral portion thereof submerged in said liquid; the imporvement comprising:
  a. blade means having an edge bearing against said planar side surface, said blade means and edge extending downwardly beyond the periphery of the disc for collecting liquid removed from the side surface of the disc and directing it along the blade toward its lower end,
    1. said blade bearing against the exposed side surface of the disc at a location where the side surface is moving in a direction having a downward component;
  b. receiving means disposed at the lower end of said blade for receiving liquid collected on said blade at the lower end thereof;
  c. a trough in which a portion of the liquid to be sampled flows in a predetermined direction and in which the disc is disposed in a plane generally parallel to said predetermined direction,
    1. said disc being mounted for rotation in a direction causing the submerged portion thereof to move in said predetermined direction of flow of said liquid;
  d. drive means connected to said disc to rotate it at a speed whereby the linear velocity of the submerged portion is lower than the velocity of the liquid flowing through said trough; and
  e. baffle means disposed partially submerged beneath the surface of said liquid and disposed upstream of the disc for deflecting particles floating on the surface of said liquid away fom the surface of the disc.

2. Apparatus according to claim 1 wherein:
  a. said trough includes wall downstream of said disc and extending transverse the direction of flow through said trough, said wall being spaced from the bottom of the trough, whereby heavy particles accumulating at the bottom of said trough are caused to flow from said trough between the bottom of said trough and said wall.

3. Apparatus according to claim 1 wherein:
  a. said blade means for removing said thin film further comprises two blades each having one edge which bears against the opposite side surfaces of said disc and each of which extends downwardly and freely beyond the periphery of the disc.

4. Apparatus according to claim 3 wherein:
  a. the disc has a thickness of about 1/16 of an inch.

5. Apparatus according to claim 4 wherein:

a. the blades oppose each other and bear against opposite opposed side surfaces of the disc; and b. the gap between the opposed blades located beyond the periphery of the disc being sufficiently small whereby liquid collected on the blades will tend to bridge across the gap.

6. Apparatus according to claim 5 wherein:

a. said gap is equal to the thickness of the disc.

* * * * *